United States Patent [19]
Epstein et al.

[11] Patent Number: 5,804,205
[45] Date of Patent: Sep. 8, 1998

[54] SKIN CARE COMPOSITIONS

[75] Inventors: Howard Epstein; Thomas Menzel, both of Rochester; Zhenze Hu, Pittsford, all of N.Y.

[73] Assignee: Bausch & Lomb Incorporated, Rochester, N.Y.

[21] Appl. No.: 732,083

[22] Filed: Oct. 16, 1996

Related U.S. Application Data

[60] Provisional application No. 60/008,852 Feb. 26, 1996.
[51] Int. Cl.$^6$ ...................................................... A61K 7/48
[52] U.S. Cl. ....................... 424/401; 424/78.08; 514/844; 514/845; 514/846; 514/937
[58] Field of Search ................................ 424/401, 78.08; 514/844–846, 937

[56] References Cited

U.S. PATENT DOCUMENTS

| | | | |
|---|---|---|---|
| 4,389,418 | 6/1983 | Burton | 424/365 |
| 4,781,918 | 11/1988 | Hofinger et al. | 424/70 |
| 5,013,763 | 5/1991 | Tubesing et al. | 514/772 |
| 5,135,748 | 8/1992 | Ziegler et al. | 424/401 |

FOREIGN PATENT DOCUMENTS

| | | |
|---|---|---|
| 0692248A1 | 1/1996 | European Pat. Off. . |
| 2555441A | 5/1985 | France . |
| 8-3016 | 1/1996 | Japan . |
| 94/03527 | 2/1994 | WIPO . |

OTHER PUBLICATIONS

Effect of High Glycerin Therapeutic Moisturizers on the Ultrastructure of the Stratum Corneum.
Orgasol—Ultrafine Polyamide Powders—Elf Atochem.
DATABASE WPI, Week 8605, Derwent Publications Ltd., London, GB; AN 86–031927 XP002024748, see abstract & JP 60252407A (Kanebo) 13 Dec. 1985.

*Primary Examiner*—Jyothsna Venkat
*Attorney, Agent, or Firm*—Chris P. Konkol

[57] ABSTRACT

The present invention is a skin care composition which provides a high degree of moisturization without leaving a "tacky" residue on treated skin. The subject composition comprises; (a) from about 2 to about 10 weight percent of a quaternary ammonium compound having the formula:

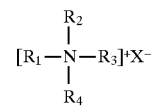

wherein $R_1$ and $R_2$ are each alkyl groups having from about 16 to about 22 carbon atoms, $R_3$ and $R_4$ are each lower alkyl groups having from about 1 to about 3 carbon atoms, and X is a salt-forming anion, (b) from about 1 to about 40 weight percent of a humectant, and (c) from about 0.01 to about 5 weight percent of non-irritating hydrophobic polymeric microspheres having an average particle size of less than about 50 microns.

8 Claims, No Drawings

SKIN CARE COMPOSITIONS

This application claims the benefit of U.S. Provisional Application No. 60/008,852 Feb. 26, 1996 now abandoned.

FIELD OF THE INVENTION

The present invention relates to skin care compositions useful for moisturizing and conditioning skin. This invention specifically relates to skin care compositions utilizing cationic emulsifiers and humectants. Specific embodiments of the subject invention include those having relatively high amounts of humectants, e.g. greater than about 20 weight percent of glycerin.

BACKGROUND

A wide variety of skin care compositions have been used to treat dry skin. Examples of such compositions include both oil-in-water, i.e. "water-out" emulsions and water-in-oil, i.e. "oil-out" emulsions. Emulsifiers utilized in these formulations have included anionic, nonionic, cationic, and mixtures thereof, although the more common commercial products have used anionic and nonionic emulsifiers.

An example of a popular skin care composition based upon cationic emulsifiers is available under the mark, Curel® from Bausch & Lomb Incorporated, (see U.S. Pat. No. 4,389,418). This product utilizes a quaternary ammonium compound as the sole emulsifying agent in an oil-in-water emulsion with about 4 weight percent petrolatum, about 12 weight percent glycerin, and various other constituents including fatty alcohols (e.g. cetyl alcohol), fatty ester emollients (e.g. isopropyl palmitate), and silicone oils (e.g. dimethicone). Other examples of skin care products using cationic surfactants are described in U.S. Pat. Nos. 4,781,918; 5,013,763; and 5,135,748.

Skin moisturizing studies have indicated a direct relationship between the amount of humectant in a skin care composition and the composition's effectiveness in moisturizing skin treated therewith. For example, it has been found that increasing amounts of glycerin (e.g. at least about 20 weight percent) in skin care compositions are more effective at moisturization, see for example Orth, D. S., et al., *Effect of High Glycerin Therapeutic Moisturizers on the Ultrastructure of the Stratum Corneum*. Although most commercial skin care compositions typically include less than about 12 weight percent glycerin, compositions with higher glycerin amounts are known.

As described in U.S. Pat. No. 4,389,418, it is particularly difficult to produce a skin care composition which effectively moisturizes without leaving a "greasy" and/or "tacky" residue on the skin. This undesirable residue associated with many skin care compositions is commonly due to petrolatum (or mineral oil) and/or humectants, e.g. glycerin, contained therein. This problem is exacerbated by increasing the relative amount of these constituents within the composition. By way of example, the skin care composition available from Bausch & Lomb Incorporated under the mark Cure'l® has about 12 weight percent glycerin and has a very desirable, non-tacky feel when applied. However, if the amount of glycerin is increased within the composition, e.g. from about 12 weight percent to about 20 weight percent, the composition has a distinct "tacky" sensation when applied.

Thus, although skin care compositions having higher concentrations of humectants (and/or petrolatum or mineral oil) are generally desired due to their increased moisturization capabilities, such compositions are typically too "tacky" and/or "greasy" to be commercially acceptable.

SUMMARY OF THE INVENTION

The present invention is a skin care composition for the treatment of skin which provides a high degree of moisturization without leaving a "tacky" or "sticky" residue on treated skin. The subject composition comprises; (a) from about 2 to about 10 weight percent of a quaternary ammonium compound having the formula:

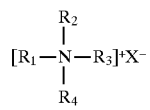

wherein $R_1$ and $R_2$ are each alkyl groups having from about 16 to about 22 carbon atoms, $R_3$ and $R_4$ are each lower alkyl groups having from about 1 to about 3 carbon atoms, and X is a salt-forming anion, (b) from about 1 to about 40 weight percent of a humectant, and (c) from about 0.01 to about 5 weight percent of non-irritating hydrophobic polymeric microspheres having an average particle size of less than about 50 microns.

Methods for treating, (e.g. moisturizing and conditioning), skin using the subject skin care composition are also disclosed.

DETAILED DESCRIPTION OF THE INVENTION

The skin care compositions of the present invention include quaternary ammonium emulsifiers having the general formula:

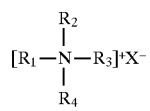

wherein $R_1$ and $R_2$ are each alkyl groups, preferably substantially linear, having from about 16 to about 22 carbon atoms; $R_3$ and $R_4$ are each lower alkyl groups having from about 1 to about 3 carbon atoms; and X is a salt-forming anion. Preferably the salt-forming anion is chloride, bromide, or iodide. The cationic emulsifiers preferably exhibit hard, waxy and non sticky characteristics. Such cationic emulsifiers are described in detail in U.S. Pat. No. 4,389,418. The most preferred cationic emulsifier is dimethyl distearyl ammonium chloride. The cationic emulsifier is preferably present in the composition of this invention in concentrations of about 2 to about 10 weight percent, preferably about 3 to 8 weight percent.

The compositions of the present invention further include humectants. Humectants act as hygroscopic agents, increasing the amount of water held in the stratum corneum and contributing to the softening of the skin surface. Suitable humectants for the formulations of this invention include but are not limited to: glycerin, propylene glycol, sorbitol, polyethylene glycol, 1,2,6-hexanetriol, hydrogenated starch hydrolysate, inositol, mannitol, PEG-5 pentaerythritol ether, polyglyceryl sorbitol, xylitol, sucrose, and combinations thereof. Glycerin is a particularly preferred humectant. The humectant is present in the composition at concentrations of about 1 to about 40 weight percent, but preferably above about 12 weight percent and still more preferably above 20 weight percent. One specific embodiment of the present invention includes about 21 weight percent glycerin.

As stated above, greater skin moisturization can be obtained by increasing the amount of humectants within the skin care compositions, above that commonly used, e.g. using above about 12 weight percent glycerin, or more preferably, above about 20 weight percent. Unfortunately, such "high moisturizing formulations" leave a tacky residue on the skin. This has been specifically identified with respect to compositions utilizing the quaternary ammonium compounds, as used in the present invention.

It has been discovered that the "tackiness" associated with high humectant concentrations can be significantly reduced by including hydrophobic polymeric microspheres within the composition. The microspheres should be non-irritating to the skin and preferably have an average particle size of less than about 50 microns. Preferred microspheres comprise polyamide materials, e.g. nylon including nylon 12, nylon 66 and nylon 6. A specific example of such a material is a polyamide powder available as "ORGASOL® 2002 D NAT COS" from Elf Atochem (Lipo Chemicals—US distributor), a nylon 12 microsphere having an average particle size of about 20 microns. These microsphere typically comprise from about 0.01 to about 5 weight percent of the subject composition, depending upon the specific type and amounts of other constituents within the compositions.

In addition to the aforementioned constituents, the subject composition may include components conventionally used in skin care formulations. Such other components include for example; (a) petrolatum or mineral oil, (b) fatty alcohols, (c) fatty ester emollients, (d) silicone oils or fluids, and (e) preservatives. These components must in general be safe for application to the human skin and must be compatible with the other components of the formulation. Selection of these components is generally within the skill of the art. The following discussion refers to components in the singular although it will be understood that combinations or mixtures are intended to be included as well.

The petrolatum or mineral oil component selected will generally be USP or NF grade. The petrolatum may be white or yellow. The viscosity or consistency grade of petrolatum is not narrowly critical. Petrolatum can be partially replaced with mixtures of hydrocarbon materials which can be formulated to resemble petrolatum in appearance and consistency. For example, mixtures of petrolatum with microcrystalline wax, paraffin wax, and the like may be melted together. Preferred mineral oils are white mineral oils having a viscosity of 6.7 to 69 centistokes at 40° C., a specific gravity (SG 15.6° C./15.6° C.) of 0.828 to 0.890, and a maximum pour point of −18° to −7° C. Still more preferred mineral oils have a viscosity of 6.7 to 17.0 centistokes at 40° C., a specific gravity of 0.828 to 0.860, and a maximum pour point of about −7° to −10° C. When used, the petrolatum or mineral oil component is included in the formulations at a concentration of about 1 to about 10 weight percent, more preferably about 2 to about 6 weight percent. Higher percentages generally cause the skin care composition to leave a "greasy" residue when applied to the skin. The previously described microspheres permit the use of higher relative percentages of petrolatum or mineral oil to be used without the noted "greasy" residue.

Fatty alcohols (typically monohydric alcohols) used in the compositions of this invention stabilize the emulsion and provide a cosmetically acceptable viscosity. Selection of the fatty alcohol is not narrowly critical although those alcohols characterized as: $C_{12}$ to $C_{32}$, preferably $C_{14}$ to $C_{22}$, substantially saturated alkanols will generally be employed. Examples include stearyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols. When used the fatty alcohol is preferably included in the formulations of this invention at a concentration within the range from about 1 to about 8 weight percent, more preferably about 2 to about 4 weight percent.

Fatty ester emollients enhance the tactile properties of the composition. Examples of suitable fatty esters for use in the formulation of this invention include isopropyl myristate, isopropyl palmitate, isopropyl isostearate, isostearyl isostearate, diisopropyl sebacate, propylene glycol dipelargonate, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty ester is isopropyl palmitate. When used the fatty ester emollient is preferably included in the formulations of this invention at a concentration of about 1 to about 8 weight percent, more preferably about 2 to about 5 weight percent.

Silicone oils or fluids may be used to improve the lubricity of the composition during application to the skin. Preferably, the viscosity of the silicone component at a temperature of 25° C. is from about 5 to about 12,500 centistokes. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane endblocked with trimethyl units, is presently preferred. Dimethicone having a viscosity between 10 and 1000 centistokes is particularly preferred. When used, the silicone oils are preferably included in the formulations of this invention at a concentration of about 0.1 to about 5 weight percent, more preferably about 1 to about 2 weight percent.

The compositions may also contain other conventional additives employed in cosmetic emulsions. Such additives include aesthetic enhancers, fragrance oils, dyes, preservatives, antioxidants, sun screen additives, and medicaments such as menthol and the like. Preferred aesthetic enhancers are polyquaternium 31 and aluminum starch octenylsuccinate. Examples of preferred antioxidants include vitamin E acetate, DL-panthenol, and ascorbyl palmitate.

The water employed in the compositions and method of this invention is preferably purified water obtained, e.g., by distilling ordinary tap water, by purifying ordinary water though an ion exchange resin, or by other techniques apparent to those skilled in the art. Water preferably accounts for about 30 to 90 weight percent, but more preferably from about 55 to 85 weight percent of the subject composition.

The compositions of the present invention may be prepared as either oil-in-water or water-in-oil emulsions.

Preferred oil-in-water emulsions are prepared by first forming an aqueous mixture of the water-soluble components, e.g. the humectant, water-soluble preservatives, followed by adding water-insoluble components. The water-insoluble components include the; cationic emulsifier, water-insoluble preservatives, petrolatum or mineral oil component, subject polymeric microspheres, fatty alcohol component, fatty ester emollient, and silicone oil component. The components are preferably added to the water in the following sequence: water-soluble preservatives, humectant, water-insoluble preservatives, petrolatum/mineral oil, fatty ester, and silicone oil. After these components are thoroughly mixed, the mixture is heated to a temperature of about 80° to 95° C. under agitation and the fatty alcohol is added, followed by the cationic emulsifier, to form a water-in-oil emulsion. After the cationic emulsifier is added, the polymeric microspheres are added under continued agitation. The input of mixing energy will be high and will be maintained for a time sufficient to form a water-in-oil emulsion having a smooth appearance (indicating the presence of relatively small micelles in the emulsion).

Water is then directly injected into the emulsion to cool it to a temperature of about 45° to about 60° C. The temperature is critical. Unstable emulsions result if the temperature drops below about 45° C. Higher temperatures promote unacceptable water loss through evaporation. During this quench step the emulsion, initially water-in-oil, inverts to form an oil-in-water emulsion. Antioxidants, if used, are typically then added to the mixture.

Water is added at two points during the process: when forming the aqueous mixture of water-insoluble components and humectant and when quenching the emulsion. The bulk of the water is added during the quench step with a minor amount added with the aqueous mixture of water-insoluble components and humectant. Preferably, about 20% of the water is added with the aqueous mixture, with the balance added during quenching.

After complete mixing and additional cooling, the mixture is filtered to produce a homogeneous lotion or cream.

As stated, the skin care compositions of the present invention are applied directly to the skin in the treatment of dry skin. The subject compositions are capable of achieving a greater degree of skin moisturization without the common tackiness associated with compositions containing relatively high percentages (e.g. above 12 weight percent, but preferably above about 20 weight percent) of humectant, particularly glycerin.

EXAMPLE

As a further illustration of the present invention, two skin care compositions were prepared, one having a formulation as provided below in Table I, the other having a substantially similar formulation but without any polymeric microspheres. The two compositions were evaluated for "tackiness" upon application to the skin. The subject composition which included the polymeric microspheres had a statistically noticeable reduction in tackiness upon application as compared with the similar composition having no polymeric microspheres.

TABLE I

| CONSTITUENT | Composition I (weight percent) |
| --- | --- |
| Purified Water | 59.5 |
| Glycerin 99.5% USP | 21.0 |
| Petrolatum White USP | 7.0 |
| Dimethyldistearylamonium Chloride (Varisoft TA-103) | 5.0 |
| Isopropyl Palmitate | 3.0 |
| Cetyl Alcohol | 2.5 |
| Dimethicone 10 CST | 1.25 |
| Orgasol 2002 | 0.50 |
| Methyl Paraben | 0.10 |
| Vitamin E acetate | 0.10 |
| Propyl Paraben | 0.04 |
| DL-Panthenol | 0.02 |
| Ascorbyl Palmitate | 0.01 |

Many other modifications and variations of the present invention are possible in light of the teachings herein. It is therefore understood that, within the scope of the claims, the present invention can be practiced other than as herein specifically described.

We claim:

1. A skin care composition in the form of an oil-in-water emulsion that provides moisturization of the skin, said composition comprising:

(a) from about 2 to about 10 weight percent of a quaternary ammonium compound having the formula

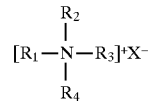

wherein $R_1$ and $R_2$ are each alkyl groups having from 16 to about 22 carbon atoms, $R_3$ and $R_4$ are each lower alkyl groups having from 1 to 3 carbon atoms and X is a salt-forming anion;

(b) from greater than about 12 to about 40 weight percent of glycerine; and (c) from about 0.01 to about 5 weight percent of non-irritating hydrophobic polymeric microspheres having an average particle size of less than 50 microns wherein said polymeric micro spheres are made from nylon.

2. The composition of claim 1 wherein said nylon is at least one of: nylon 12 and nylon 6.

3. The composition of claim 1 wherein said polymeric microspheres have an average particles size of about 20 microns.

4. The composition of claim 1 comprising greater than about 20 weight percent glycerin.

5. The composition of claim 1 wherein said composition comprises:

(a) from about 2 to about 10 weight percent of dimethyl distearyl ammonium chloride;

(b) from greater than about 12 to about 40 weight percent of glycerin;

(c) from about 0.1 to about 5 weight percent of nylon microspheres having an average particle size of less than 50 microns; and (d) from about 1 to about 10 weight percent of petrolatum or mineral oil.

6. A method for moisturizing or conditioning skin by applying a skin care composition in the form of an oil-in-water emulsion directly thereto, wherein the skin care composition comprises:

(a) from about 2 to about 10 weight percent of a quaternary ammonium compound having the formula

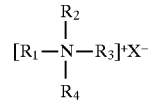

wherein $R_1$ and $R_2$ are each alkyl groups having from 16 to about 22 carbon atoms, $R_3$ and $R_4$ are each lower alkyl groups having from 1 to 3 carbon atoms and X is a salt-forming anion;

(b) from greater than about 12 to about 40 weight percent of glycerine; and (c) from about 0.01 to about 5 weight percent of non-irritating hydrophobic polymeric microspheres having an average particle size of less than 50 microns wherein said polymeric micro spheres are made from nylon.

7. The method of claim 6 wherein the composition comprises greater than about 20 weight percent glycerin.

8. The method of claim 6 wherein the composition comprises:
(a) from about 2 to about 10 weight percent of dimethyl distearyl ammonium chloride;
(b) greater than about 20 weight percent of glycerin;
(c) from about 0.1 to about 5 weight percent of nylon microspheres having an average particle size of less than 50 microns; and
(d) from about 1 to about 10 weight percent of petrolatum or mineral oil.

* * * * *